United States Patent
Watanabe

(10) Patent No.: US 7,655,478 B2
(45) Date of Patent: Feb. 2, 2010

(54) SENSOR DEVICE, SENSING METHOD, BIOLOGICAL SUBSTANCE SENSOR DEVICE, BIOLOGICAL SUBSTANCE SENSING METHOD, SECRETION SENSOR DEVICE, SECRETION SENSING METHOD, EMOTION SENSOR DEVICE AND EMOTION SENSING METHOD

(75) Inventor: Yuuki Watanabe, Tokyo (JP)

(73) Assignee: Sony Corporation, Tokyo (JP)

(*) Notice: Subject to any disclaimer, the term of this patent is extended or adjusted under 35 U.S.C. 154(b) by 478 days.

(21) Appl. No.: 10/821,554

(22) Filed: Apr. 9, 2004

(65) Prior Publication Data
US 2004/0235055 A1 Nov. 25, 2004

(30) Foreign Application Priority Data
Apr. 10, 2003 (JP) ............... P2003-106313

(51) Int. Cl.
*G01N 33/551* (2006.01)
*G01N 33/552* (2006.01)
*G01N 33/553* (2006.01)

(52) U.S. Cl. ............... 436/524; 310/311; 310/312; 310/313 R; 385/12; 385/129; 385/130; 422/82.11; 435/287.2; 435/288.7; 436/518; 436/525; 436/527; 436/805

(58) Field of Classification Search ............... None
See application file for complete search history.

(56) References Cited

U.S. PATENT DOCUMENTS

| | | | | |
|---|---|---|---|---|
| 4,487,839 A | * | 12/1984 | Kamentsky | 436/518 |
| 5,492,840 A | * | 2/1996 | Malmqvist et al. | 436/518 |
| 5,629,213 A | * | 5/1997 | Kornguth et al. | 436/518 |
| 6,630,309 B2 | * | 10/2003 | Willner et al. | 435/7.1 |

FOREIGN PATENT DOCUMENTS

| | | |
|---|---|---|
| JP | 2000-055920 | 2/2000 |
| JP | 2001-091416 | 4/2001 |
| JP | 2002-168860 | 6/2002 |
| JP | 2002-181700 | 6/2002 |

OTHER PUBLICATIONS

Japanese Office Action issued on Apr. 1, 2008.

* cited by examiner

*Primary Examiner*—Christopher L Chin
(74) *Attorney, Agent, or Firm*—Sonnenschein Nath & Rosenthal LLP

(57) ABSTRACT

In a sensor device and a sensing method capable of simultaneously extracting plural pieces of information including information about the presence/absence, distribution, and so on, of targets, in case of measuring changes in nature of a detecting portion (11) upon coupling with targets (a and b), information about changes in quantities of the targets (a and b) with time is extracted in addition to information about the presence/absence, distribution, and so on, of the targets (a and b) from geometrical structures of the detecting portion (11), such as locations and/or shapes of bonding sites (A and B) for selectively coupling with the targets (a and b), respectively.

10 Claims, 12 Drawing Sheets

SENSOR DEVICE, SENSING METHOD, BIOLOGICAL SUBSTANCE SENSOR DEVICE, BIOLOGICAL SUBSTANCE SENSING METHOD, SECRETION SENSOR DEVICE, SECRETION SENSING METHOD, EMOTION SENSOR DEVICE AND EMOTION SENSING METHOD

RELATED APPLICATION DATA

The present application claims priority to Japanese Application(s) No(s). P2003-106313 filed Apr. 10, 2003, which application(s) is/are incorporated herein by reference to the extent permitted by law.

BACKGROUND OF THE INVENTION

1. Field of the Invention

The present invention relates to a sensor device, sensing method, biological substance sensor device, biological substance sensing method, secretion sensor device, secretion sensing method, emotion sensor device and emotion sensing method that are especially suitable for application to measurement of emotion by detecting changes in secretory amount of a secretion product caused by human mental movements.

2. Description of the Related Art

The modern information society is rapidly establishing its ground concerning transmission of information by communication and holding of information by storage. The most important techniques requested upon the ground are considered to be directed to two issues, namely, how to ingest which effective kind of information, and how to transfer the information to people. Sensors are one of techniques for the former issue. The sensor technology, however, is also considered a basic technique necessary for effective transfer that is the latter issue.

Many sensors have been developed heretofore (Kiyoshi Takahashi et al.: "Sensor no Jiten (Dictionary of Sensors)", Asakura Shoten, 1991; Kinji Koshitani: "Zukai de Wakaru Sensor no Hanashi (Illustrated Story of Sensors)", Nippon Jitsugyo Publishing Co., Ltd., 1995). These sensors can be roughly divided to three categories, namely, physical sensors, chemical sensors and biosensors in terms of their measurement principles. A wide variety of sensors have been known, such as photo sensors and temperature sensors as physical sensors, ion sensors and gas sensors as chemical sensors, and DNA sensors and immune sensors as biosensors. They also have a broad range of applications, but most of them have the disadvantage that each has a single function and can measure only one piece of information each time.

As a technique to cope with the above-indicated disadvantage, the concept of sensor fusion is now under researches (Hiroo Yamazaki and Masatoshi Ishikawa: "Sensor Fusion: Jissekai no Noudouteki Rikai to Chiteki Kousei (Sensor Fusion: Active Understanding of Its Real World and Intellectual Reconstruction)", Corona Publishing Co., Ltd., 1992). Sensor fusion pertains to simultaneously ingesting a variety of sensor information and appropriately processing them to extract information that cannot be obtained with a single sensor.

Also known are sensors of a type configured to measure information of a system variable in nature by combination of target physical objects (N. Hoshimiya: "Seitai Jouhou Keisoku (Biological information Measurement)", Morikita Shuppan Co., Ltd., 1997). There are some different types of sensor linkage sites depending upon natures of targets. To deal with proteins as the target, the use of antibody/antigen reaction and the use of metal nanoparticles with appropriate linkers bonded have been reported (Christof M. Niemeyer: "Nanoparticles, Proteins, and Nucleic Acids: Biotechnology Meets Materials Science", Angew. Chem. Int. Ed. 2001, 40, 4128-4158). To deal with DNA chains as the targets, there is a proposal of winding DNA chains having base sequence sites complementary to the targets on metal nanoparticles (Christof M. Niemeyer: "Nanoparticles, Proteins, and Nucleic Acids: Biotechnology Meets Materials Science", Angew. Chem. Int. Ed. 2001, 40, 4128-4158). To deal with DNA chains as the targets, there is another proposal of fixing one end of complementary DNA to a substrate and fixing a metal nanoparticle to the other end (A. Yamaguchi, S. Juodkazis, S. Matsuo, and H. Misawa; "Enhancement of surface plasmon resonance sensing of DNA hybridization using colloidal Au attached probe DNA, Chem. Lett.", p. 190 (2002)).

It is also known that stress has a certain relation to the central nerve system, automatic nerve system, endocrine system and immune system (Hiroshi Miyata as editor: "Shin Seiri Shinrigaku 1 (New Physiological Psychology 1)", Kitaoji Shobo, 1998, pp 281-282).

Further, there are proposed methods of measuring stress or emotion from a secretion product (Japanese Patent Laid-open JP-2002-188996-A2; Japanese Patent Laid-open JP-2002-168860-A; Japanese Patent Laid-open JP-H10-239312-A).

The sensor fusion, however, is a technique directed mainly to enabling human intellectual recognition and formation of a concept, and it is not a technique for measuring different pieces of information from various aspects of a single target. Therefore, for applications other than high-order functions such as intellectual procedures, heavy processing load is considered to become a problem.

OBJECTS AND SUMMARY OF THE INVENTION

It is therefore an object of the invention to provide a sensor device and a sensing method capable of simultaneously extracting pieces of information including information about the presence/absence, distribution, and so on, of targets.

Another object of the invention is to provide a biological substance sensor device, a biological substance sensing method, a secretion product sensor device and a secretion product sensing method capable of simultaneously extracting pieces of information including information about the presence/absence, distribution, and so on, of biological substances or secretion product products.

Still another object of the invention is to provide an emotion sensor device and an emotion sensing method capable of simultaneously extracting pieces of information including information about the presence/absence, distribution, and so on, of secretion product products secreted from a living body upon emotional changes and thereby measuring emotional changes.

According to the first aspect of the invention, there is provided a sensor device for measuring changes in nature of a detecting portion upon coupling with a target, characterized in extracting plural pieces of information including information about the presence/absence, distribution, and so on, of the target by using spatial structure of the detecting portion.

According to the second aspect of the invention, there is provided a sensing method for measuring changes in nature of a detecting portion upon coupling with a target, comprising:

extracting plural pieces of information including information about the presence/absence, distribution, and so on, of the target by the use of a spatial structure of the detecting portion.

In the first and second aspects of the invention, a typical spatial structure of the detector portion is a geometrical structure. The geometrical structure can be, for example, the layout or configuration of the binding sites, or their statistical distribution (for example, distribution of positional offsets or configurations in case it is intended to align the binding sites in form of regular lattices). Possible binding forces that may contribute to the coupling between targets and detector portions are Van der Waals' forces, electrostatic attraction forces (coulomb forces) and hydrogen bonding, and one or more of them may contribute to the coupling. Typically, a detector portion has a plurality of bonding sites, and individual targets selectively couple with individual bonding sites. These bonding sites are appropriately arranged either periodically or aperiodically in accordance with the targets. Both periodical portions and aperiodical portions may be mixed as well. Alternatively, without designating information on alignment, information on distribution of binding sites may be given. These binding sites are typically arranged in alignment with sizes of a plurality of targets, and a time change in amount of the targets is detected by making out a steric hindrance by using a difference in size among these targets. In case the differences in size among these targets are too small to detect time changes in amount of these targets only from the arrangement of the binding sites, the detector portions may be formed with steps on their detection surfaces to enable detection of time changes of the targets by making steric hindrance from the steps. It is also possible to make steric hindrance by making a kind of binding sites on metal nanoparticles. Information is generally extracted by measuring changes of physical features or structures of the detector portions caused by their coupling with the targets. A preferable physical feature for easier measurement is the dielectric constant or weight of the detector portion. The structure may be a conformation of molecules such as proteins, and steric hindrance or the like occurs upon changes in conformation.

Appropriate binding sites are used in accordance with the targets. For example, in case the target is immunoglobulin, antibody can be used as the binding site. That is, the relation of antibody and antigen may be established between the target and the binding site to use the coupling of the antibody and the antigen by antigen-antibody reaction. In case the target is a protein, metal nanoparticles with adequate linkers coupled may be used as the binding sites (Christof M. Niemeyer: "Nanoparticles, Proteins, and Nucleic Acids: Biotechnology Meets Materials Science", Angew. Chem. Int. Ed. 2001, 40, 4128-4158). In case the target is a nerve transmitter substance (for example, acetylcholine), its receptor (for example, acetylcholine receptor) may be used as the binding sites.

Changes in dielectric constant of the detector portion by the coupling of the target can be detected easily by using the principle of surface plasmon resonance (SPR). Sensors using surface plasmon resonance (SPR sensor) can sensitively measure changes of such a system. An example of SPR sensors has a structure of three layers including a binding site, substrate and prism, and measures the coupling of the target from changes of the total reflection critical angle of incident light caused by the coupling of the target. In this case, changes in dielectric coefficient by the coupling of the target contribute to changes of the total reflection critical angle. More specifically, incident light totally reflects at a certain critical angle on the interface between the prism portion having a higher refractive index and the substrate portion having a lower refractive index. Then, evanescent light corresponding to the critical angle of the total reflection appears on the interface, and when it adequately couples with the surface plasmon that is the compressional wave of conduction electrons of the substrate, surface plasmon resonance occurs. In case the target couples with the binding site, surface plasmon changes following to effective changes of the refractive index within the reach of the evanescent light, and the critical angle inducing surface plasmon resonance varies. Responsively, in case of a DNA chains measuring model, for example, the sensor detects changes of the dielectric constant of the system caused by the coupling of DNA in the former case, or the sensor detects changes of the dielectric constant of the system caused by movements of metal nanoparticles closer to the substrate due to reduction of the chain length when DNA becomes double-stranded in the latter case.

Changes in weight of the detector portion caused by the coupling with the target can be detected easily by using an oscillating circuit and a frequency-measuring device. That is, it is possible to use an oscillation type sensor configured to measure the changes in weight of the detector portion upon the coupling of the target with the detector portion through changes in vibration occurring when certain vibration is continuously applied to the substrate. This is a technique effective when the system does not change so much in dielectric constant before and after the coupling.

According to the third aspect of the invention, there is provided a biological substance sensor device for measuring changes in nature of a detecting portion upon coupling a biological substance, characterized in simultaneously extracting plural pieces of information including information about the presence/absence, distribution, and so on, of the biological substance from a spatial structure of the detecting portion.

According to the fourth aspect of the invention, there is provided a biological substance sensing method for measuring changes in nature of a detecting portion upon coupling a biological substance, comprising:

simultaneously extracting plural pieces of information including information about the presence/absence, distribution, and so on, of the biological substance from a spatial structure of the detecting portion.

In the third and fourth aspects of the invention, the biological substance contemplates a variety of proteins and DNA. Secretion products are a kind of biological substances.

The foregoing statement in conjunction with the first and second aspects of the invention is applicable to the third and fourth aspects of the invention as far as it is consistent with their natures.

According to the fifth aspect of the invention, there is provided a secretion sensor device for measuring changes in nature of a detecting portion upon coupling with a secretion product, characterized in simultaneously extracting plural pieces of information including information about the presence/absence, distribution, and so on, of the secretion product from a spatial structure of the detecting portion.

According to the sixth aspect of the invention, there is provided a secretion sensing method for measuring changes in nature of a detecting portion upon coupling with a secretion product, comprising:

simultaneously extracting plural pieces of information including information about the presence/absence, distribution, and so on, of the secretion product from a spatial structure of the detecting portion.

In the fifth and sixth aspects of the invention, the secretion product basically contemplates any kinds of secretion products that are secreted from living bodies.

The foregoing statement in conjunction with the first and second aspects of the invention is applicable to the fifth and sixth aspects of the invention as far as it is consistent with their natures.

According to the seventh aspect of the invention, there is provided an emotion sensor device for detecting changes in emotion through measurement of changes in nature of a detecting portion upon coupling with a secretion product secreted from a living body along with changes of the emotion, characterized in simultaneously extracting plural pieces of information including information about the presence/absence, distribution, and so on, of the secretion product from a spatial structure of the detecting portion.

According to the eighth aspect of the invention, there is provided an emotion sensing method for detecting changes in emotion through measurement of changes in nature of a detecting portion upon coupling with a secretion product secreted from a living body along with changes of the emotion, comprising:

simultaneously extracting plural pieces of information including information about the presence/absence, distribution, and so on, of the secretion product from a spatial structure of the detecting portion.

In the seventh and eighth aspects of the invention, the emotion pertains to any of all emotive or affective process when mental activities are divided to intelligence, feeling and consciousness. Thus, the emotion may be emotional movements, tempers, feelings, or the like. Mental stress is also contemplated here. For example, the emotion varies with various kinds of external stimulation (such as visual simulation), and it is followed by changes in amount of secretion from endocrine systems. Therefore, changes of the emotion can be measured through changes of the amount of secretion. Specific examples of endocrine systems related to mental stress, for example, are referred to in some literatures (Hiroshi Miyata as editor: "Shin Seiri Shinrigaku 1 (New Physiological Psychology 1)", Kitaoji Shobo, 1998, pp 281-282; Hiroshi Miyata as editor: "Shin Seiri Shinrigaku 3 (New Physiological Psychology 3)", Kitaoji Shobo, 1998, pp 42 and 37).

The foregoing statement in conjunction with the first and second aspects of the invention is applicable to the fifth and sixth aspects of the invention as far as it is consistent with their natures.

According to the invention having the above-summarized configuration, it is possible to extract information about the presence/absence, distribution, and so on, of the target in a system to be measured, as well as information about changes with time of the amount of the target in the system by measuring with the target by way of the spatial structure of the detector portion, in particular, such as the geometrical structure of the detector portion like the location and configuration of the bonding site. Consequently, it is also possible to measure biological substances or secretion products, for example, and to measure the emotion through measurement of secretion products.

DETAILED DESCRIPTION OF THE PREFERRED EMBODIMENTS

Preferred embodiments of the present invention will now be explained below with reference to the drawings.

First explained is a sensor according to the first embodiment of the invention.

In case the distribution of a plurality of substances (targets) existing in a system to be measure changes depending upon the condition of the system, a sensor for measuring the distribution of the substances and changes of the distribution with time is important. Here is provided a sensor structure capable of measuring information about the distribution of two kinds of substances of a system as well as information about changes of the abundance ratio or the substances.

Figure 1:
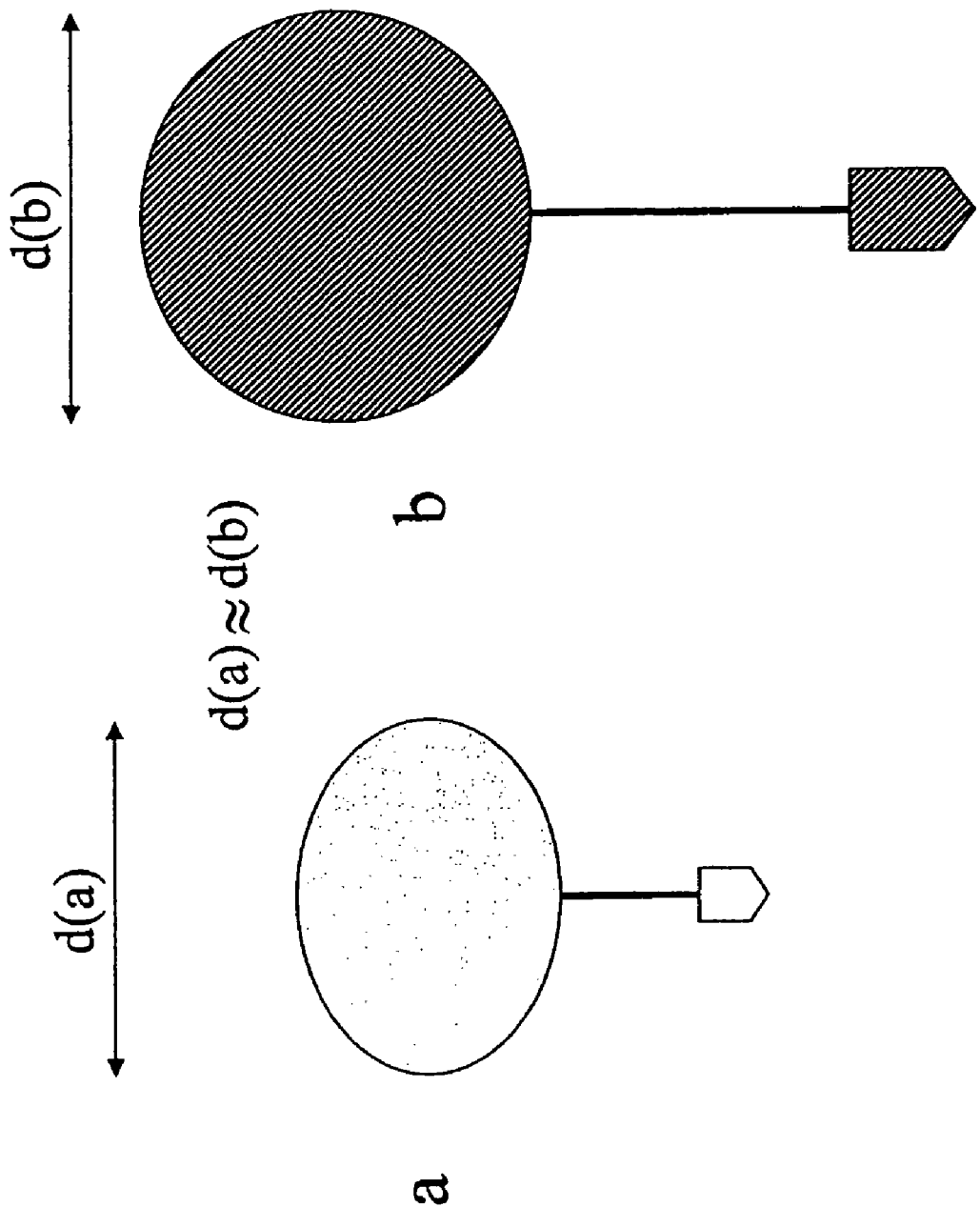
FIG. 1 is a schematic diagram showing targets to be measured by a sensor according to the first embodiment of the invention.

Here is taken the most simple example in which two kinds of targets a and b having shapes shown in FIG. 1 should be measured. Assume that these targets a and b have approximately equal sizes d(a) and d(b). In the direction normal to the d(a) and d(b), however, sizes of the targets a and b are considerably different by the ratio shown in FIG. 1.

Figure 2:
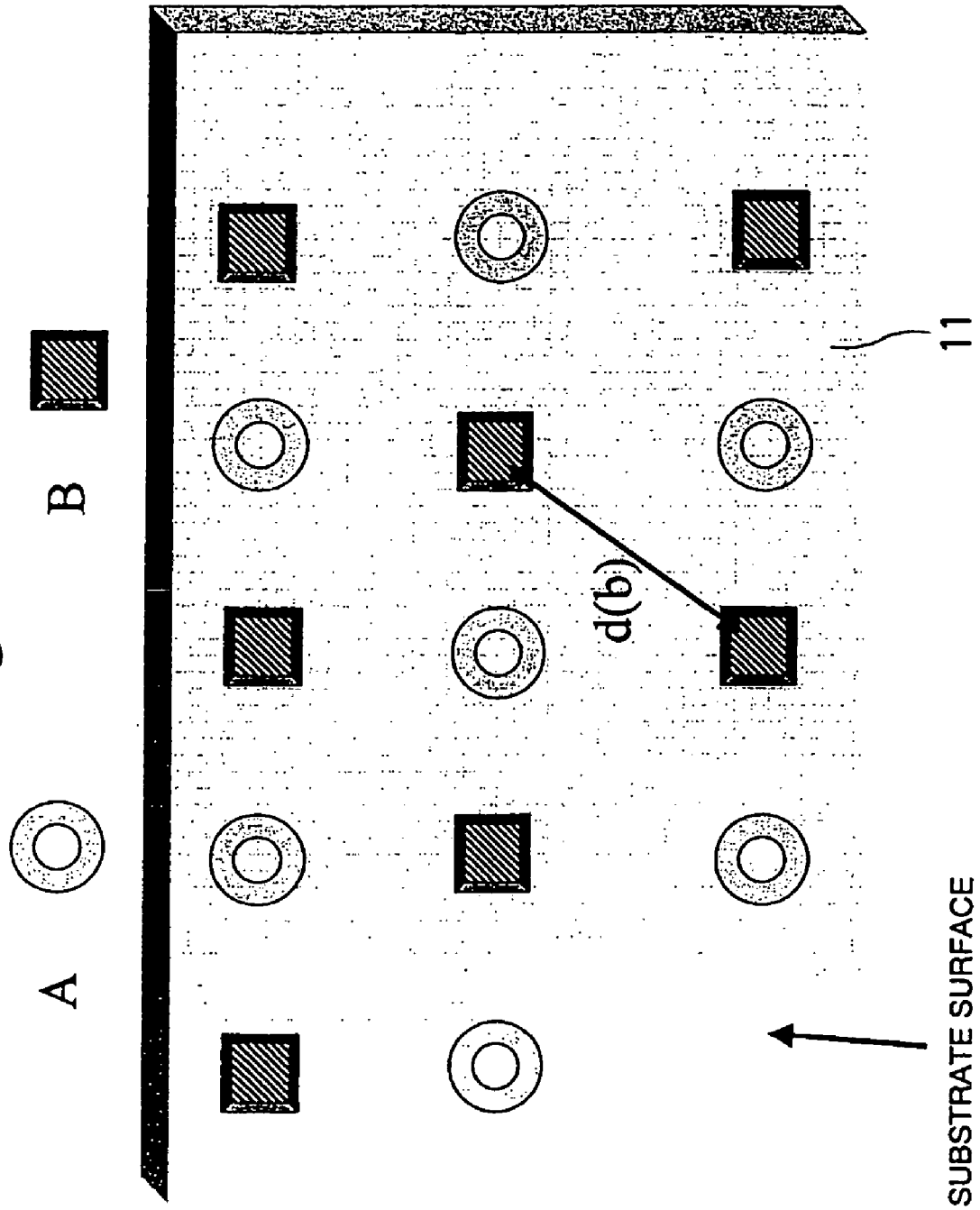
FIG. 2 is a schematic diagram showing a substrate having an arrangement of bonding sites of the sensor according to the first embodiment of the invention.

As shown in FIG. 2, the sensor has two kinds of bonding sites A and B arranged on one of major surfaces (top surface) of a substrate 11 in appropriately alternate positions to permit the targets a and b to bond them selectively. In this example, these bonding sites A and B are periodically aligned to make a face-centered plane lattice when each kind of bonding sites A or B is remarked. In case the targets a and b couple with the bonding sites independently from each other, distance between the nearest bonding sites A and distance of the nearest bonding sites B are determined so that the targets a can simultaneously couple with all of the bonding sites A under no steric hindrance and the targets b can simultaneously couple with all of the bonding sites B under no steric hindrance. More specifically, distance between the nearest bonding sites A and distance between the nearest bonding sites B are determined slightly larger than d(a) and d(b) respectively.

Combinations of the targets a and b with the bonding sites A and B are adequately selected depending upon the natures of the targets a and b. More specifically, in case the targets a and b are immunoglobulin, combination of antibody and antigen that specifically couple by antigen/antibody reaction, or combination using metal nanoparticles having coupled linkers, can e uses (Christof M. Niemeyer: "Nanoparticles, Proteins, and Nucleic Acids: Biotechnology Meets Materials Science", Angew. Chem. Int. Ed. 2001, 40, 4128-4158).

Next explained are ways of using the sensor having the above-explained configuration.

First set is a sensor in a system (a liquid phase or a gas phase) containing the targets a and b.

Figure 3:
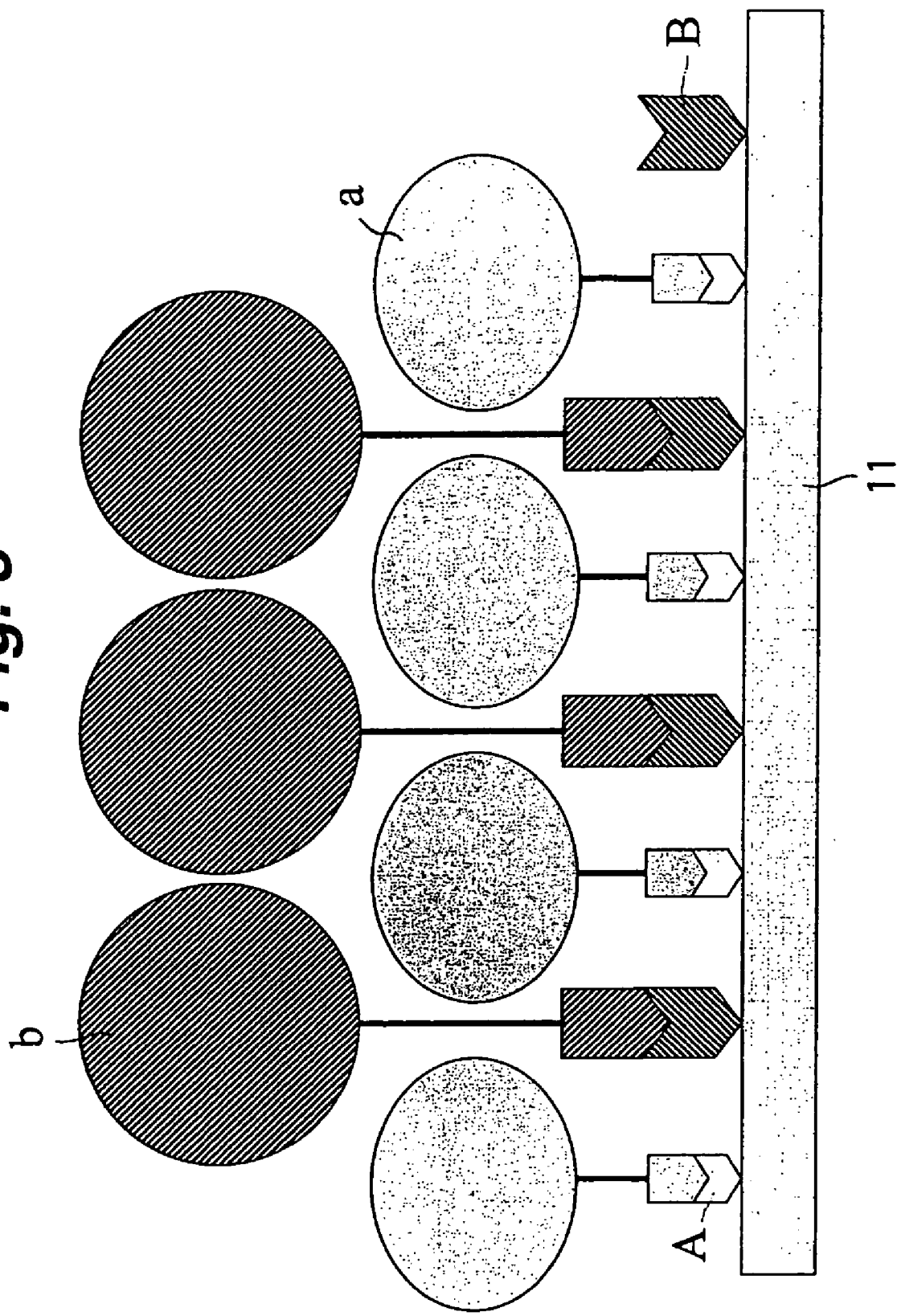
FIG. 3 is a schematic diagram for explaining a way of using the sensor according to the first embodiment of the invention.

In this setting, assume that the abundance ratio of the targets a is first higher but the abundance ratio of the targets b increases later. In this case, the majority targets a couple with the bonding sites A of the substrate, and thereafter, the targets b couple the binding sites B under no steric hindrance as shown in FIG. 3.

Figure 4:
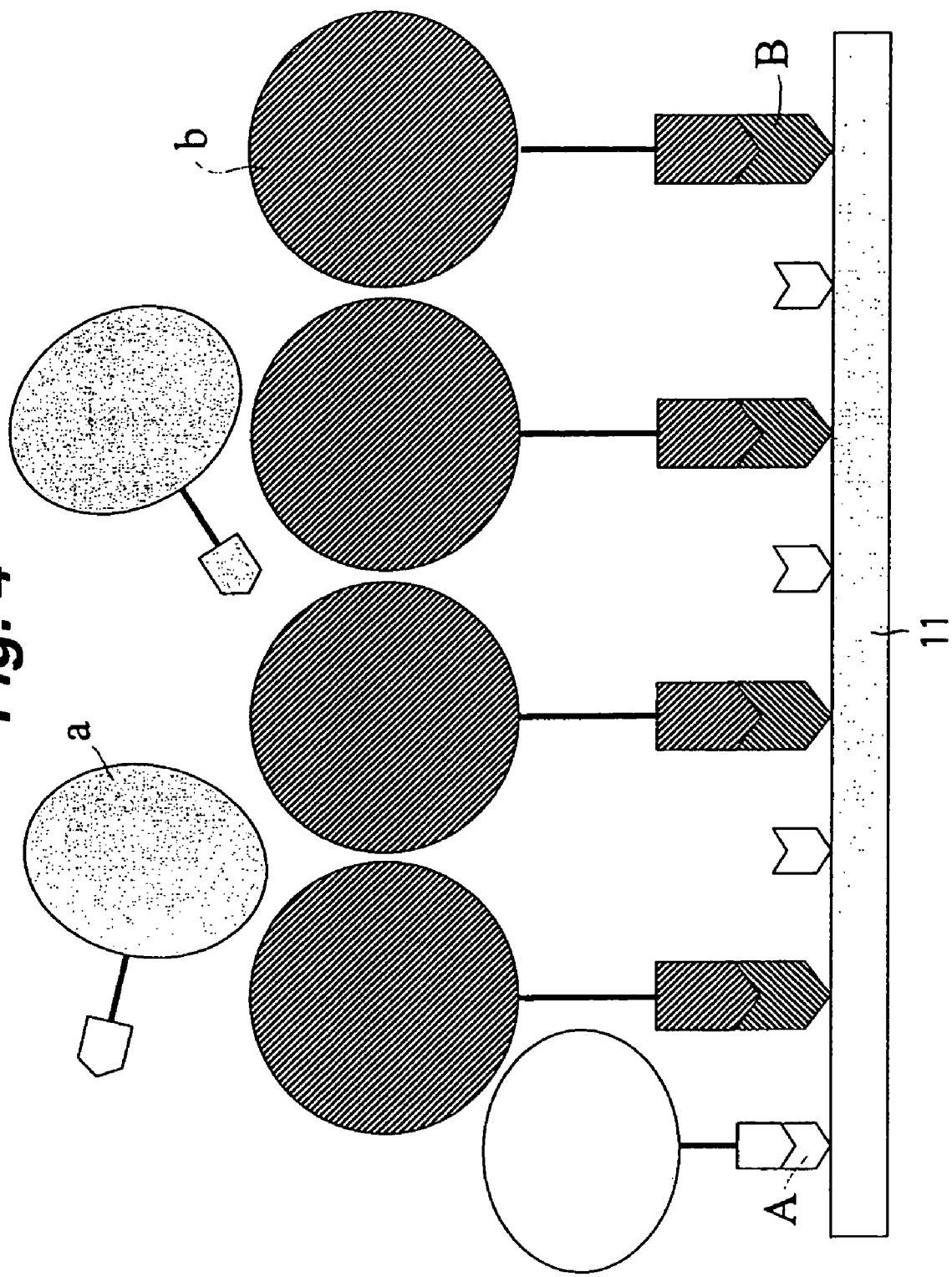
FIG. 4 is a schematic diagram for explaining a way of using the sensor according to the first embodiment of the invention.

Next assume the opposite condition where the abundance ratio of the targets b is higher and the abundance ratio of the targets a increases later. In this case, as shown in FIG. 4, the binding sites B and the targets b having coupled earlier become steric hindrance, and the targets a that have increased later hardly couple with the bonding sites A. Therefore, by measuring this difference, it is possible to specify changes of the system condition with time, namely, whether the targets a were first the majority and the targets b increased later, or whether the targets b were first the majority and the targets a increased later.

In order to measure the difference between those two conditions, an SPR sensor may be used if the targets a and b are different in dielectric constant, or a quartz-oscillating sensor may be used if the targets a and b are different in weight.

Figure 5:
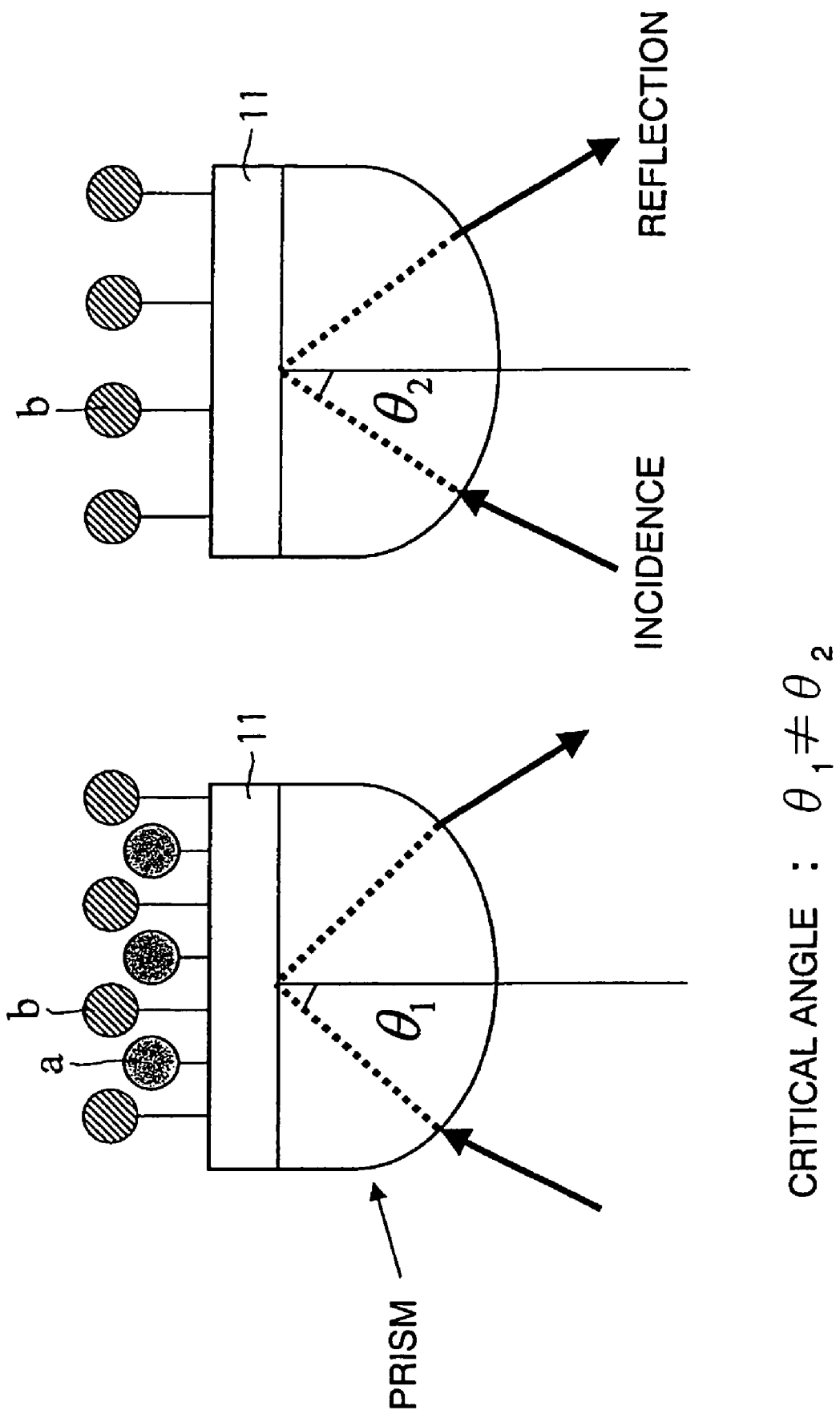
FIG. 5 is a schematic diagram for explaining a way of using the sensor according to the first embodiment of the invention.

FIG. 5 shows an example of measurement using an SPR sensor. The SPR sensor comprises a prism 12 for contact with the other major surface (rear surface) of the substrate 11 to introduce monochromatic light such as laser light into the prism 12 from outside. In case both the targets a and b have coupled as shown in the left diagram of FIG. 5, SPR occurs when incident light enters the other major surface of the substrate 11 by the incidence angle equal to the critical angle. In this case, since $\theta_1 \neq \theta_2$ (in this case, $\theta_1 > \theta_2$), by measuring this difference, it is possible to easily distinguish whether both the targets a and b have already coupled with the former major surface of the substrate 11 or only the targets b have coupled.

As explained above, according to the first embodiment, by placing the binding sites A and B for selective coupling with the targets a and b to be measured at appropriate positions in appropriate intervals and observing the process of coupling of the targets a and b with the binding sites A and B, it is possible to extract information on changes in abundance ratio of the targets a and b with time in addition to information on the presence/absence, distribution, and so on, of the targets a and b. That is, by controls of the geometric structure of the detection surface of the substrate 11, geometric information regarding the targets a and b can be processed inside the sensor, and many pieces of information processed in necessary forms can be extracted.

Next explained is a sensor according to the second embodiment of the invention. This sensor is suitable for use when differences in shape and size between the targets a and b to be measured are not so large.

Figure 6:
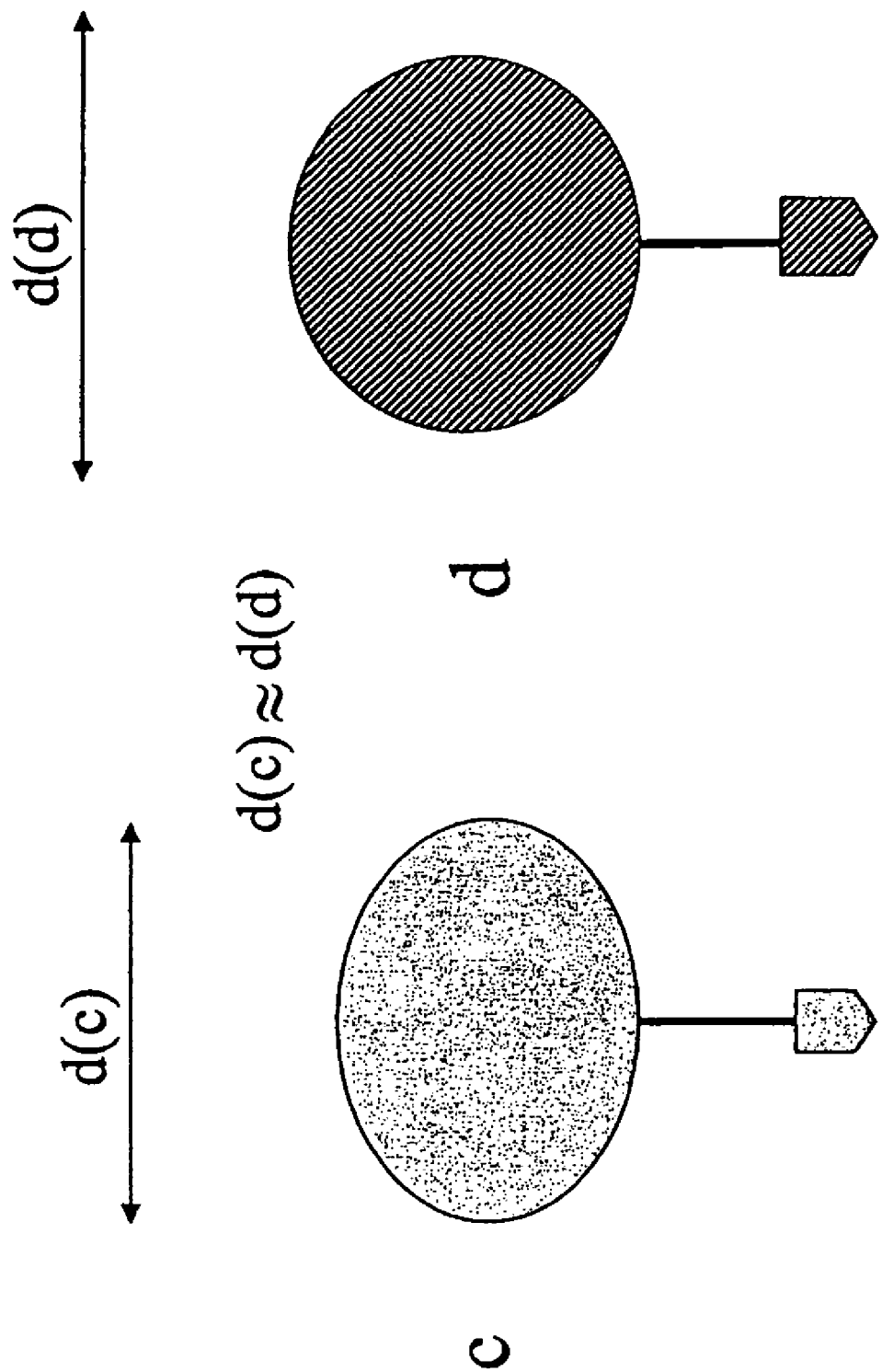
FIG. 6 is a schematic diagram showing targets to be measured by a sensor according to the second embodiment of the invention.

In the second embodiment, assume that two kinds of targets c and d having shapes as shown in FIG. 6 should be measured. Let the targets c and d have sizes d(c) and d(d) that are substantially equal. In this case, their sizes are approximately equal also in the direction normal to d(c) and d(d).

Figure 7:
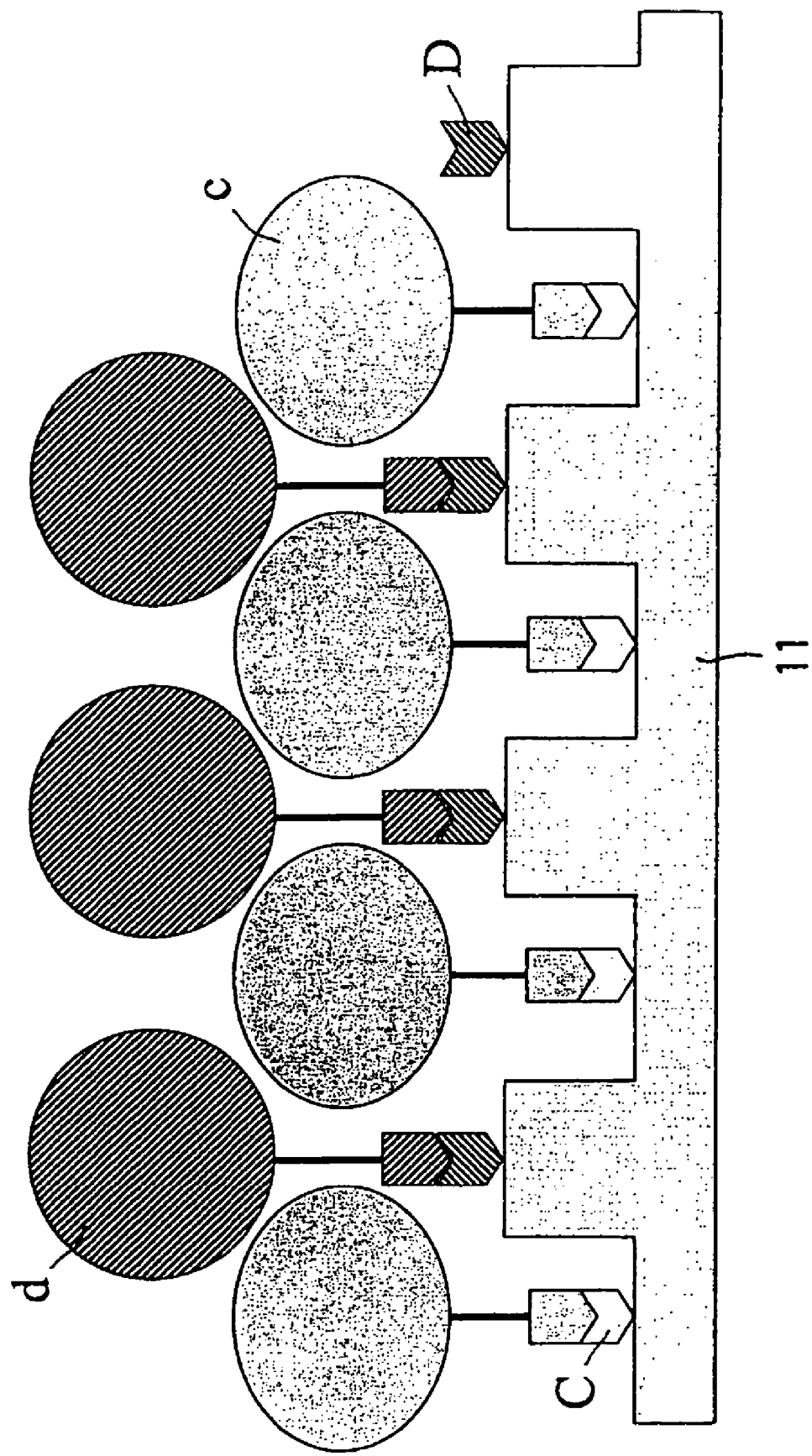
FIG. 7 is a schematic diagram for explaining a way of using the sensor according to the second embodiment of the invention.

As shown in FIG. 7, the sensor has two kinds of bonding sits C and D capable of selectively coupling with the targets c and d, which are alternately arranged at appropriate positions on one major surface of the substrate 11, similarly to the first embodiment. In the second embodiment, however, the sensor has recesses 12 formed by nanoprocessing to have a rectangular cross section at locations on one major surface of the substrate corresponding to the bonding sites C. The bonding sites C reside at bottoms of the recesses 12, and the bonding sites D reside on banks of the recesses 12, unlike the first embodiment.

Next explained is a way of using the sensor having the above-explained configuration.

First set is the sensor on the system containing the targets c and d.

In this setting, assume that the targets c first exist by a higher abundance ratio, and the targets d increase its abundance ratio later. In this case, as shown in FIG. 7, the majority targets c first couple with the binding sites C of the substrate 11. Thereafter, the targets d also couple with the binding sites D under no steric hindrance.

Figure 8:
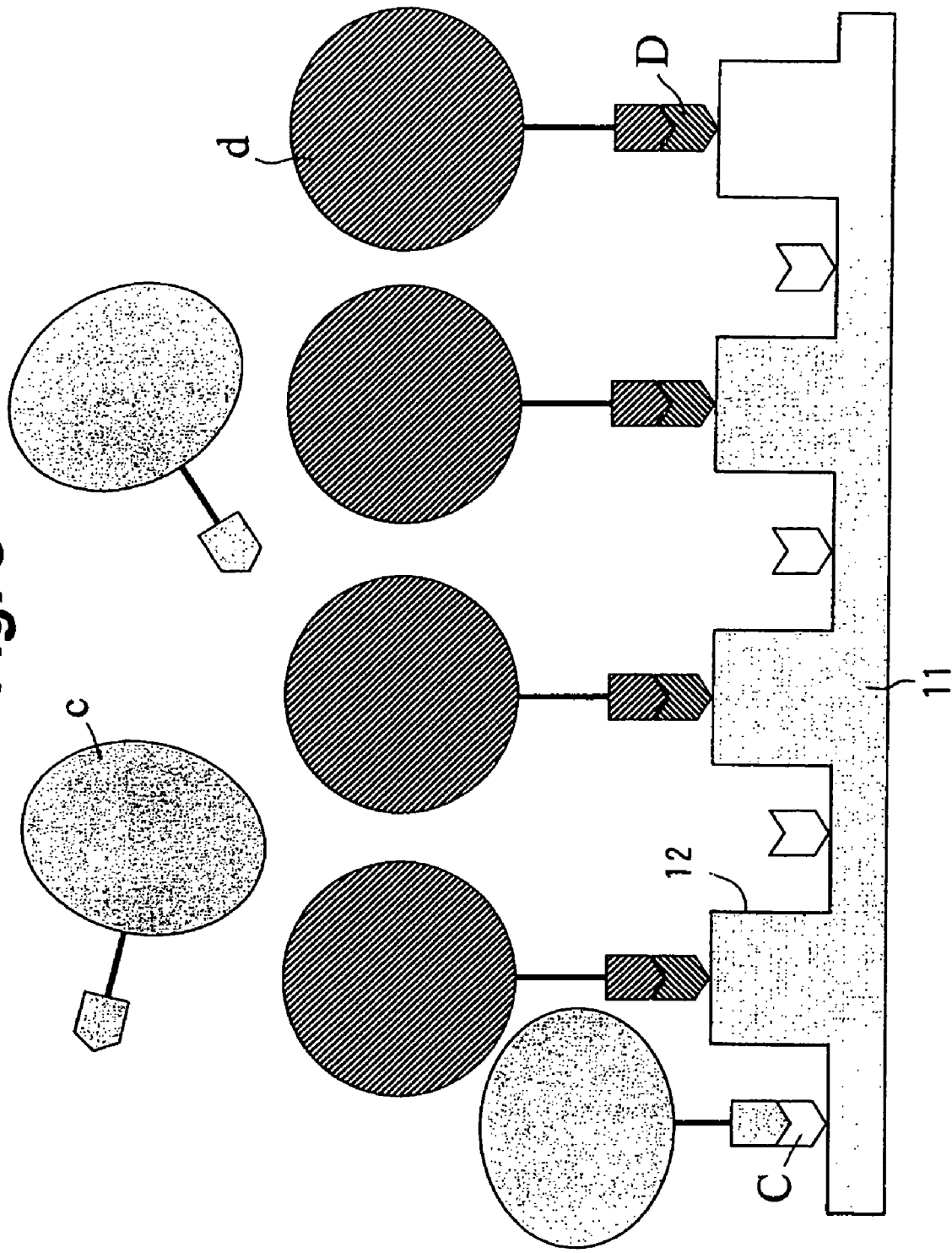
FIG. 8 is a schematic diagram for explaining a way of using the sensor according to the second embodiment of the invention.

Next assume the opposite condition where that the targets d first have a higher abundance ratio, and the targets c increase its abundance ratio later. In this case, as shown in FIG. 8, the binding sites D and the targets d having coupled earlier become steric hindrance, and the targets c that have increased later hardly couple with the bonding sites C. Therefore, by measuring this difference, it is possible to specify changes of the system condition with time, namely, whether the targets c were first the majority and the targets d increased later, or whether the targets d were first the majority and the targets c increased later.

In the other respects, the second embodiment is the same as the first embodiment, and their explanation is omitted here to avoid redundancy.

Figure 9:
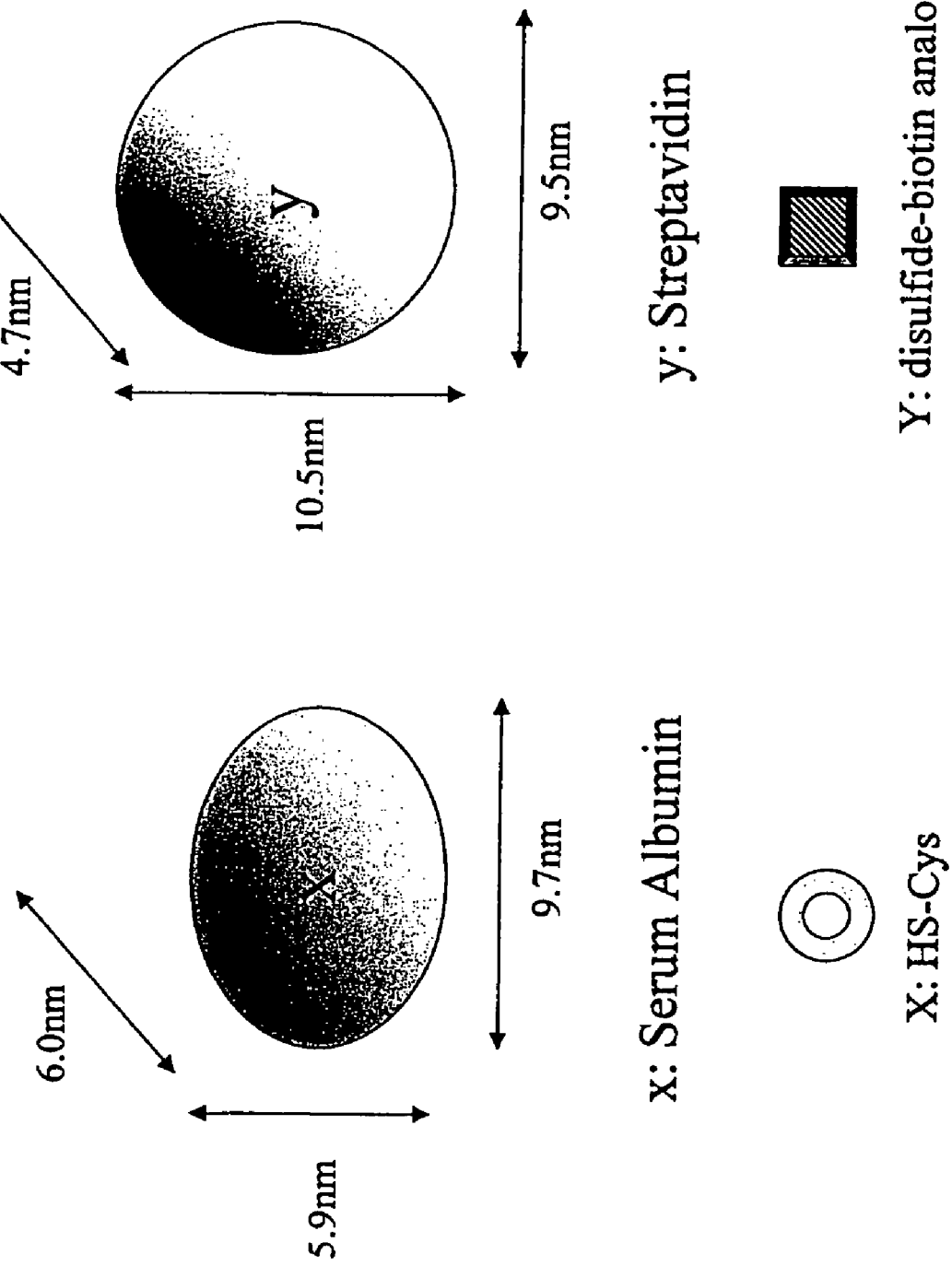
FIG. 9 is a schematic diagram showing targets to be measured in a sensor according to the third embodiment of the invention.
Figure 10:
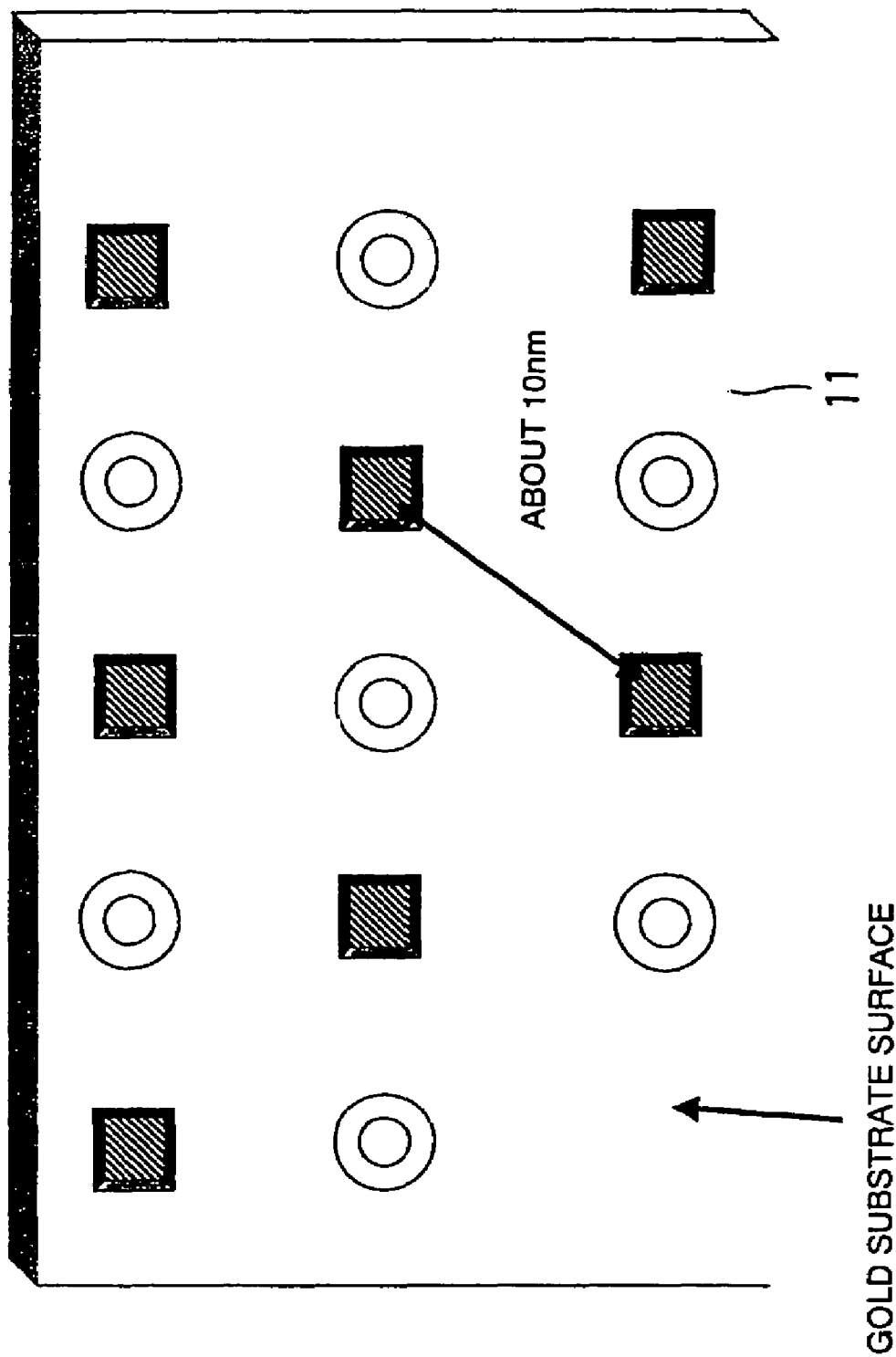
FIG. 10 is a schematic diagram showing an exemplary substrate having an arrangement of bonding sites of the sensor according to the second embodiment of the invention.
Figure 11:
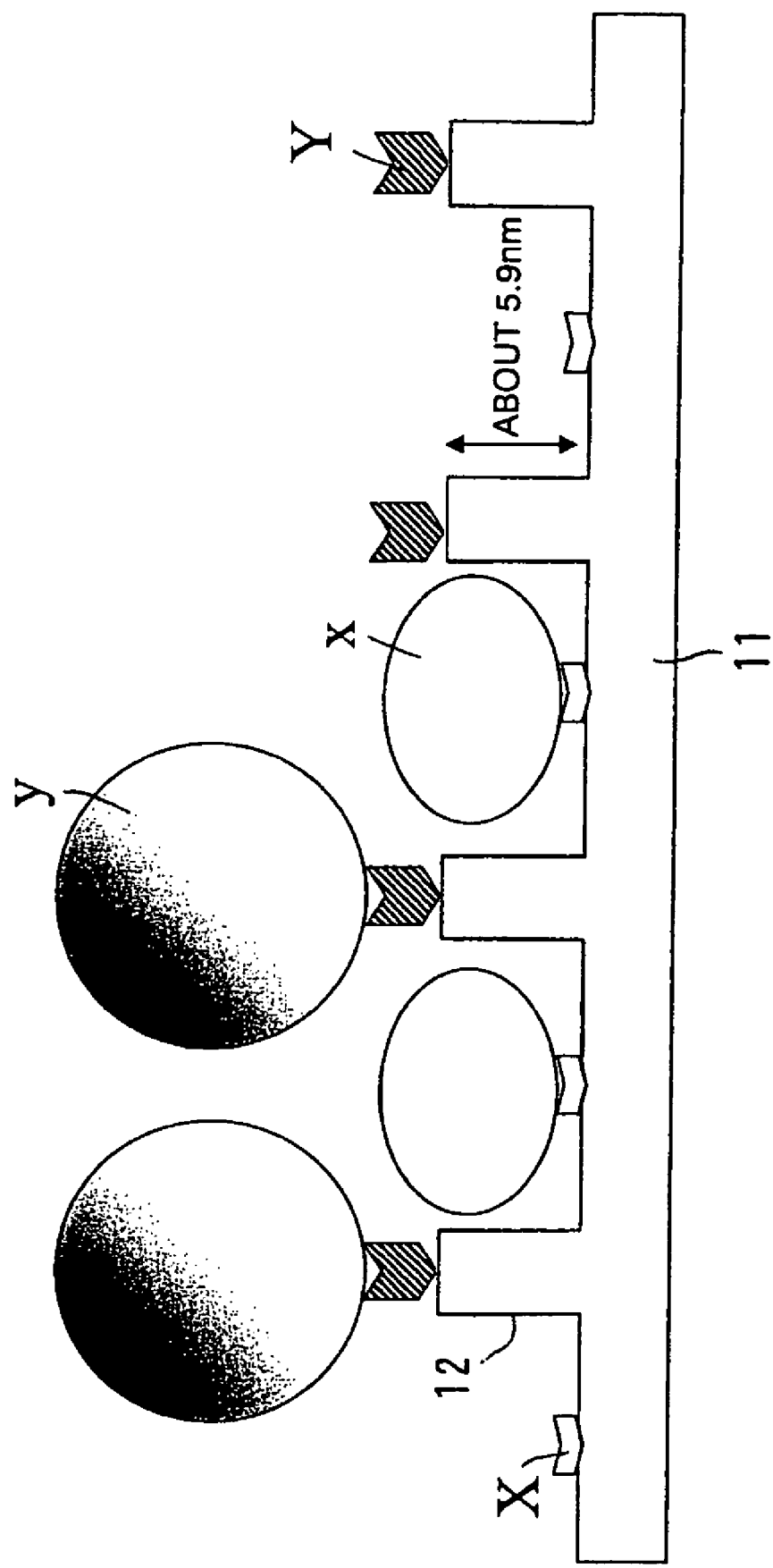
FIG. 11 is a schematic diagram showing that the targets shown in FIG. 9 have bonded to the bonding sites of the substrate shown in FIG. 10.

FIG. 9 shows an example of the targets c and d and the binding sites C and D. In this example, the targets c and d are x: serum albumin and y: streptavidin, respectively, and the binding cites C and D are X:HS-Cys and Y: disulfide-biotin analogue. They have sizes as shown in FIG. 9. The substrate 11 is a gold substrate, and X and Y are bound to the gold substrate by thiol, for example. Furthermore, as shown in FIG. 10, distance between the nearest binding sites C and distance between the nearest binding sites D are approximately 10 nm. FIG. 11 is a diagram corresponding to FIG. 7, and x couples with X and y couples with Y.

The second embodiment assures the same advantages as those of the first embodiment even when the targets c and d to be measured are approximately equal in shape and size.

Figure 12:
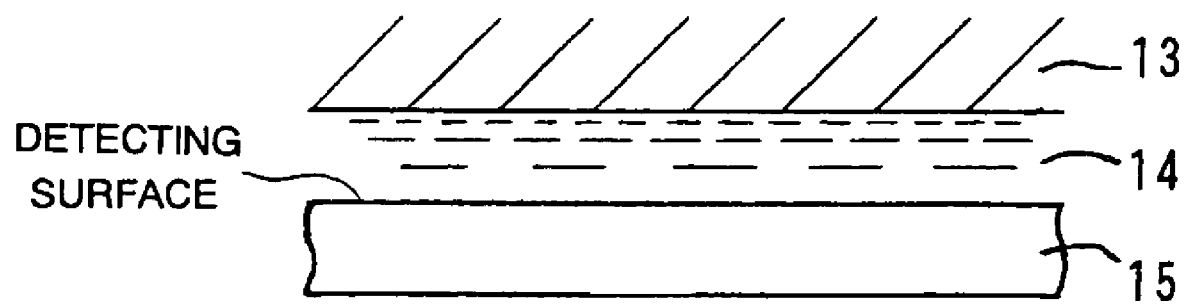
FIG. 12 is a schematic diagram showing an aspect of sensing by the sensor according to the first embodiment or the second embodiment of the invention.

FIG. 12 shows an aspect of sensing using the sensor according to the first embodiment and the sensor according to the second embodiment to detect a secretion product from a living body. As shown in FIG. 12, a secretion 14 secreted from a living body 13 contacts the detecting surface of the sensor 15. The living body 13 may be a tongue, and saliva is secreted from salivary glands. Since saliva contains immunoglobulin among others, the immunoglobulin can be detected Heretofore, some specific embodiments have been explained. However, the invention is not limited to these embodiments, but it contemplates various changes and modifications not departing from its technical concept.

For example, numerical values, structures, locations, shapes, materials, and so on, which have been shown in conjunction with those embodiments, are only examples, and other appropriate numerical values, structures, locations, shapes, materials, and so on, may be used wherever necessary.

As described above, the present invention is effective for measuring changes in nature of the detecting portion upon coupling with targets, and can simultaneously extracts plural pieces of information including information about the presence/absence, distribution, and so on, of targets.

What is claimed is:

1. A sensor device which measures changes in a detecting portion upon coupling with a system containing at least two targets, the sensor device comprising:
   a sensing portion including an oscillating circuit and a frequency measuring device in combination with a surface plasmon resonance circuit; and
   a detecting portion having a plurality of binding sites, each binding site permitting one type of a plurality of different types of the targets to selectively couple therewith, wherein,
      the sensing portion extracts plural pieces of information including information about at least the presence, absence, or distribution of each type of target via coupling of each target with the detecting portion which is effective to determine if a steric hindrance exists, and
      the sensing portion extracts said information by measuring changes in the weight of the detecting portion upon coupling with the targets.

2. The sensor device according to claim 1 wherein the binding sites couple with the targets to detect changes in amount of the targets with time.

3. The sensor device according to claim 1 wherein said information is extracted by measuring changes in physical nature or structure of the detecting portion upon coupling with the targets.

4. The sensor device according to claim 1 wherein said information is extracted by measuring changes in dielectric constant of the detecting portion upon coupling with the targets.

5. The sensor device according to claim 1 wherein the targets are antigens and binding sites are antibodies, and the antigens and the antibodies couple by antigen/antibody reaction.

6. A sensing method for measuring changes in a system containing at least two targets upon coupling with a detecting portion, comprising:
   selectively coupling the targets to one of a plurality of binding sites on the detecting portion;
   extracting information including information about at least the presence, absence, or distribution of each of the targets via coupling of the targets with the detecting portion using a sensing portion which includes an oscillating circuit and a frequency measuring device in combination with a surface plasmon resonance; and
   determining if a steric hindrance exists due to a change in presence, absence, or distribution of each of the targets over time,
   wherein,
      the sensing portion extracts said information by measuring changes in the weight of the detecting portion upon coupling with the targets.

7. A biological substance sensor device for measuring changes in a biological substance containing at least two targets upon coupling with a detecting portion, the biological substance sensor device comprising:
   a sensing portion including an oscillating circuit and a frequency measuring device in combination with a surface plasmon resonance; and
   a detecting portion,
   wherein,
      the biological substance sensor device simultaneously extracts plural pieces of information including information about the, presence, absence, or distribution of the targets via selective coupling of the targets with the detecting portion which is effective to determine if a steric hindrance exists, and
      the sensing portion extracts said information by measuring changes in the weight of the detecting portion upon coupling with the targets.

8. A biological substance sensing method for measuring changes in a biological substance containing at least two targets upon coupling of the biological substance with a detecting portion, comprising:
   providing the biological substance for coupling with the detecting portion;
   simultaneously extracting plural pieces of information including information about at least the presence, absence, or distribution each of the targets via selective coupling of the targets with the detecting portion using a sensing portion which includes an oscillating circuit and a frequency measuring device in combination with a surface plasmon resonance, and
   determining if a steric hindrance exists due to a change in presence, absence, or distribution of each of the targets over time,
   wherein,
      the sensing portion extracts said information by measuring changes in the weight of the detecting portion upon coupling with the targets.

9. A secretion sensor device for measuring changes in a secretion product upon coupling with a detecting portion, the secretion sensor device comprising:
   a sensing portion including an oscillating circuit and a frequency measuring device in combination with a surface plasmon resonance
   a detecting portion,
   wherein,
      the sensing portion extracts plural pieces of information including information about the presence, absence, or distribution of the secretion product via selective coupling of the product with the detecting portion which is effective to determine if a steric hindrance exists,
   wherein,
      the sensing portion extracts said information by measuring changes in the weight of the detecting portion upon coupling with the targets.

10. A secretion sensing method for measuring changes in a secretion product containing at least two targets upon coupling with a detecting portion, comprising:
   providing the secretion product for coupling with the detecting portion;
   simultaneously extracting plural pieces of information including information about at least the presence, absence, or distribution each of the targets via selective coupling of the targets with the detecting portion using a sensing portion which includes an oscillating circuit and a frequency measuring device in combination with a surface plasmon resonance, and
   determining if a steric hindrance exists due to a change in presence, absence, or distribution of each of the targets of the targets over time,
   wherein,
      said information is extracted by measuring changes in the weight of the detecting portion upon coupling with the targets.

* * * * *